United States Patent [19]

Czogalla

[11] Patent Number: 4,876,361
[45] Date of Patent: Oct. 24, 1989

[54] PROCESS FOR THE PRODUCTION OF THIOPHENES FROM ALPHA-METHYLENE KETONES IN THE SINGLE-STAGE PROCESS AND NEW ORTHO-FUSED THIOPHENES PRODUCED BY MEANS OF THE PROCESS

[75] Inventor: Claus-D. Czogalla, Feldkirchen-Westerham, Fed. Rep. of Germany

[73] Assignee: Rita von der Haar-Czogalla, Feldkirchen-Westerham, Fed. Rep. of Germany

[21] Appl. No.: 129,701

[22] Filed: Dec. 7, 1987

[30] Foreign Application Priority Data

Dec. 22, 1986 [DE] Fed. Rep. of Germany ....... 3643983

[51] Int. Cl.$^4$ ........................................... C07D 333/50
[52] U.S. Cl. ......................................... 549/41; 549/43
[58] Field of Search ..................................... 549/41, 43

[56] References Cited

U.S. PATENT DOCUMENTS 4,219,657  8/1980  Berger et al. .......................... 549/43

FOREIGN PATENT DOCUMENTS 250273   12/1987  European Pat. Off. .
3643983   6/1988  Fed. Rep. of Germany ........ 549/41
837725    6/1960  United Kingdom .

OTHER PUBLICATIONS

Claus-Detlef Czogalla et al., "Schwefelverbindungen Des Erdöls XI Eine Eintopfsynthese Fur 2,5-Diphenylthiophene Und b,d-Anellierte Thiophene Aus Methylenketonen", Phosphorus and Sulfur, vol. 35, pp. 127–131 (1988).

H. D. Hartough et al., Compounds with Condensed Thiophene Rings, Interscience Publishers, Inc., N.Y., title page (1954).

Chemical Abstracts, vol. 99, p. 534, Abstract 139146q (1983).

F. Boberg et al., Liebigs Annalen Der Chemie, Nr. 9, pp. 1598–1607 (1983).

Claus-Detlef Czogalla et al., Sulfur Reports, "Sulfur Compounds in Fossil Fuels I", vol. 3, pp. 121–170, Jul. 1983.

John Ashby et al., Advanced Heterocycl. Chem., "Recent Advances in the Chemistry of Dibenzothiophenes", vol. 16, pp. 214–217 (1974).

Scholz et al., Z. Chem., 7. Jg. (1967), Helt 9, p. 351.

Primary Examiner—Mary C. Lee
Assistant Examiner—E. Brenda Magrab
Attorney, Agent, or Firm—Spencer & Frank

[57] ABSTRACT

Described is a novel process which can be carried out as a single-stage synthesis for the production of substituted and/or b,d- ortho-fused thiophenes. Serving as starting compounds and α-methylene ketones which are reacted in an preferably alcoholic solvent with bromine whereafter the formed intermediate product after separation from the solvent is reacted directly with a sulphurising agent. Preferably under reflux conditions in a suitable solvent to form the end product.

In this way also hitherto unknown ortho-fused thiophene compounds are synthesized more especially those with 5 or 9 rings condensed with one another.

22 Claims, No Drawings

PROCESS FOR THE PRODUCTION OF THIOPHENES FROM ALPHA-METHYLENE KETONES IN THE SINGLE-STAGE PROCESS AND NEW ORTHO-FUSED THIOPHENES PRODUCED BY MEANS OF THE PROCESS

Substituted thiophenes and b.d-ortho-fused thiophenes are of particular interest for use in various fields, more especially as reference materials in the analysis of sulphur-containing substances of fossil raw materials, such as mineral oils, coal, carbonaceous oils, shale oils and tar sands, as model systems for studying the desulphurisation of the aforementioned fossil raw materials, also on a technical scale, as oxidation inhibitors, for example in lubricants, as active substances in the fields involving biocides, and pharmaceuticals, where the thiophenes carry certain substituents or functional groups, as monomeric units for the production of polymers, provided the thiophenes comprise certain functional groups.

A comprehensive representation of the usual and hitherto generally multi-stage processes for the production of such thiophenes is to be found in the monography of H. D. Hartough and S. L. Meisel "Compounds with condensed thiophene rings". Wiley (Interscience), New York 1954.

These processes are frequently based on starting compounds which are costly to produce or on those which have unpleasant properties as for example thiols, and the yields often leave much to be desired. Simple thiophene syntheses for example direct sulphurisation of suitable starting compounds, or sulphurisation with addition of AlCl₃, or thermolysis of suitable 1,2,3-thiadiazoles, only produce small yields and/or isomeric mixtures. The result of these circumstances is that thiophenes are very costly to produce so that only the following 5 compounds are obtainable:

100 g: 160. DM

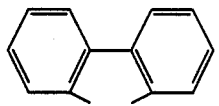
100 g: 110. DM

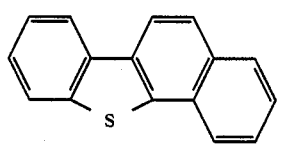
0,1 g: 65.

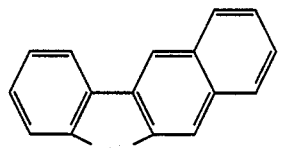
0,1 g: 200. DM

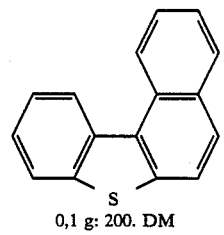
0,1 g: 200. DM

Consequently, it was the object of the invention to discover a thiophene synthesis which does not have the aforementioned disadvantages, but on the contrary has the following advantages as compared with the prior known processes:

(1) The thiophenes are to be capable of being produced in the best possible manner in a single-stage synthesis with good yields;

(2) The starting materials for the thiophene synthesis are to be easy to produce or to be commercially available and to present a large band width within a group of substances;

(3) The isolation and the preparation in pure form of the thiophenes is to be as simple as possible and is to yield pure products, also in relatively large quantities for example for technical studies.

This object is achieved according to the invention.

It has in fact surprisingly been found that with the reaction of α-methylene ketones (via the intermediate stage of 2-bromo-1-ketones as Synthon) with known sulphurising agents such as $P_4S_{10}$ or Lawessons reagent (LR), thiophenes are formed and in fact symmetrically substituted thiophenes of b.d-orthofused thiophenes; it being possible for this synthesis to be carried out as a single-stage process. It was not possible to foresee this possibility of reaction because one would inevitably expect the formation of 2-bromo-1-thioketones as final products.

The process according to the invention for the production of substituted thiophenes and/or b.d-orthofused thiophenes is accordingly characterised in that an α-methylene ketone is reacted in a polar solvent with bromine the solvent is separated out and then the 2-bromo-1-ketone which is formed is directly reacted with a sulphurising agent in a solvent and thereafter the reaction product which is formed is isolated in a manner known per se.

Diagram 1

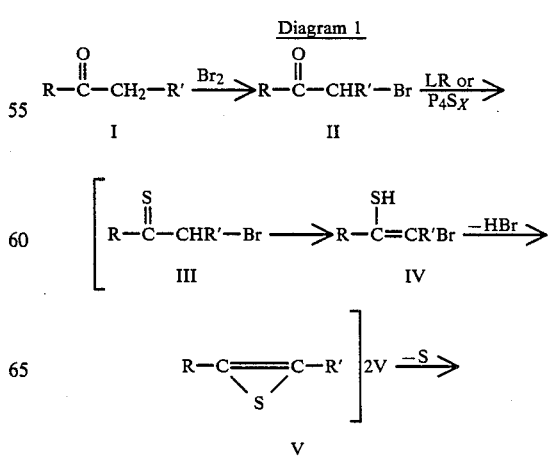

-continued
Diagram 1

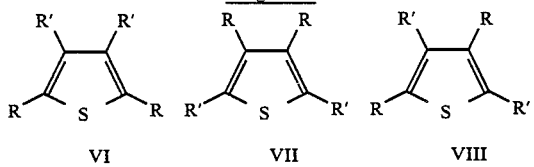

VI  VII  VIII

R,R': Alkyl, Aryl, Cycloalkyl, Ortho-fused Systems

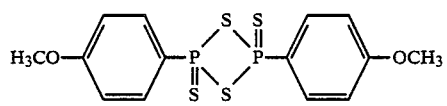

LR: LAWESSONS REAGENT

The thiophene synthesis according to the invention starts from easily available α-methylene ketones of the type of arylmethyl ketones such as acetophenones, or from hydroaromatic five-ring ketones, six-ring ketones or seven-ring ketones as for example the 1-indanones, 1-acenaphthenones, 1-tetralones, tetrahydrobenzanthracenones or hydroheteroaromatic ketones such as tetrahydrobenzothiophenones or from benzosuberones. The ketones as starting materials for the thiophene synthesis may also be substituted. Suitable as substituents are for example linear or branched alkyl groups, methoxy groups, masked amino- and carbonyl groups.

The ketones which are used are reacted in the single-stage synthesis in a manner known per se, in polar solvents, for example, in alcohols such as methanol, with $Br_2$ to form 2-bromo-1-ketones. Other suitable polar solvents are ether, glacial acetic acid, chloroform and tetrahydrofuran. Solvents which are especially suitable are low molecular weight alcohols with 1 to 4 carbon atoms, for example methanol or ethanol.

After separation of the solvent, the formed intermediate product, without further purification, is reacted with a sulphurising agent as known per se, until the evolution of HBr ceases.

What is formed are the symmetrically substituted thiophenes according to the invention, as for example 2,5-diphenyl thiophenes (from acetophenones) or symmetrically orthofused thiophenes as for example diindeno/b.d/thiophenes (from 1-indanones) all of the type VI (cf. diagram 1).

In accordance with a preferred embodiment, there is used as sulphurising agent a phosphorus-sulphur compound of the formula $P_4S_x$, in which x has the value 3, 5, 7, 9 or 10, while the solvent used is an aromatic hydrocarbon or pyridine. Suitable aromatic hydrocarbons are, for example, toluene, benzene and xylene.

In this connection it is preferred to use a molar ratio of sulphurising agent to ketone in the range from 0.1:1 to 1.5:1.

In accordance with another preferred embodiment, the sulphurising agent which is used is Lawessons reagent and the solvent is an aromatic hydrocarbon or pyridine. Aromatic hydrocarbons, benzene, toluene and xylene are also especially suitable in this connection.

It is preferred in this connection to use a molar ratio of sulphurising agent to ketone in the range from 0.5:1 to 1.5:1.

However, it is also possible to use as sulphurising agent, a phosphorus-sulphur compound of the formula $P_4S_x$, in which x has the value 3, 5, 7, 9 or 10 in combination with $Na_2S$, $NaHCO_3$ or $Na_2CO_3$ as catalyst and a polar solvent. Polar solvents which are suitable for this purpose are tetrahydrofuran, diethylene glycol dimethylether or ether.

Other suitable sulphurising agents are silicon disulphide or boron sulphide ($B_2S_3$) preferably using as solvent, chloroform or an aromatic hydrocarbon and also 0,0-diethyl dithiophosphoric acid.

The reaction with the sulphurising agent is more suitably carried out under reflux conditions, at temperatures up to 200° C.

Examples of the thiophenes which are produced in this manner are shown in Table I. The thiophenes Nos. 9 ($R_x$=OCH$_3$), 10, 12, 13 and 14 which are listed in the Table are new. As regards the thiophenes Nos. 12, 13 and 14, it has still not been possible for the indicated structure to be confirmed by X-ray structure analysis. However, in view of the progressions of the individual reactions as indicated in the reaction diagram, it is regarded as probable. In addition, the physical characteristic data confirm the existence of the compounds as such.

TABLE 1

| α-Methylene ketones | Thiophenes of type VI |
|---|---|
| ![ketone 1] C—CH₃ / O  (1) | ![thiophene 8]  (8) |
| $R_x$—[indanone] O  (2a–2c) | $R_x$—[diindeno thiophene]—$R_x$  (9a–9c) |

TABLE 1-continued

| α-Methylene ketones | Thiophenes of type VI |
|---|---|
| 3a–3d | 10a–10d |
| 4 | 11 |
| 5 | 12 |
| 6 | 13 |
| 7 | 14 |

$R_x$: H. alkyl. $OCH_3$
$R_4$. $R_5$. $R_8$: H. alkyl.

The thiophenes which can be produced according to the invention are also of interest, insofar as they can be desulphurised by means of processes which are known per se to coupled systems, for example to biphenylene or may even be provided with certain substituents which have chromophoric properties, and the are able to be used in the fields involving bleaches and dyestuffs.

In addition, the b.d-ortho-fused thiophenes which can be produced in accordance with the invention are also able to be dehydrogenated by means of known processes to provide the corresponding unsaturated compounds i.e. for example:

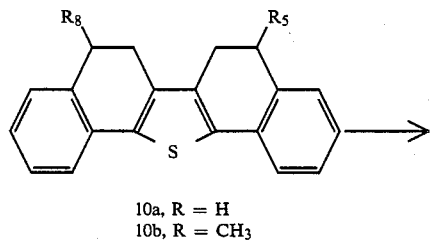

10a, R = H
10b, R = $CH_3$

-continued

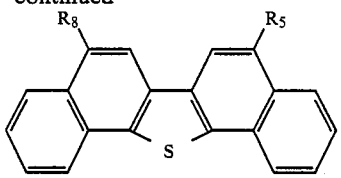

15a, R = H
15b, R = CH₃

The advantages which can be produced with the novel thiophene synthesis as compared with the syntheses according to the prior art may be summarised as follows:

Broad band widths as regards the thiophene systems which can be produced it being readily possible to build up multi-ring systems as for example compound 14 with nine rings;

production in technical quantities, such as for example compound 10a which may easily be synthesised in quantities of kilograms.

It is a particular feature of the thiophene synthesis according to the invention that instead of the three isomeric thiophenes which, according to diagram 1, can result as a mixture theoretically in equal quantities it is in practice only the thiophene VI which is isolated in preparatively relevant quantities. It either precipitates from the reaction solution or it may be easily separated by column chromatography: (The isomers VII–VIII are only capable of being detected with GC or HPLC, provided reference substances are available).

The thiophenes which can be produced according to the invention are able to be used in various spheres. They may serve as:

reference substances in the analysis of sulphur-containing substances of fossil initial substances or materials, basic systems for studying desulphurisation of fossil initial materials or substances also on a technical scale or basis, oxidation inhibitors for example in lubricants, active substances in the sphere of biocides and pharmacology provided the thiophene systems carry specific substituents or specific functional groups on the ortho-fused rings, monomeric units for the production of polymers with specified properties for example resistance to high temperature provided the thiophenes carry certain substituents or functional groups.

The invention is explained by the following examples.

Experimental section:

The 2-bromo-1-ketones are prepared by the Hauptmann method (cf. S. Hauptmann M. Scholz, I. Stopp and M. Stopp "Z. Chem." 7, 351 (1967)) by bromination of the starting ketones (0.025 mol) using 0.025 mol of bromine in methanol and are not isolated. After termination of the reaction, the methanol is removed by rotation, using the rotary piston evaporator (12 mm. Hg) the residue is taken up in dry benzene. Lawessons reagent (0.02 mol) is added and boiling takes place under reflux and with exclusion of moisture until the evolution of HBr has been completed. The reaction mixture is allowed to cool, the precipitate is filtered off with suction, washed with methanol and recrystallised. When the reaction product does not precipitate concentration is carried out and the residue is subjected to chromatography on 40×2 cm silica gel (65 g) with toluene and then with cyclohexane/CH₂Cl₂ (4:1). After working up in the usual manner recrystallisation takes place.

Reproduced in the following Table II are the initial ketones the produced thiophenes with their melting points the yield and also the empirical molecular formula of the compound in question, the results of the elementary analysis and the characterisation by data of the ¹H-NMR-spectra and the IR spectra.

The compound Nos. 8, 9a and 11 are known and the structural identity thereof was verified by comparison with the data of authentic compounds (mixed melting point IR spectra).

The compounds 10a and 10b were transformed by means of dehydrogenation into the aromatic compounds of similar structure and the structure thereof was established.

TABLE 2

Thiophenes from α-Methyleneketone

| | | Yield |
|---|---|---|
| ![ketone 1] | ![thiophene 8] | 12% |
| 1 | 8 | |
| ![indanone 2] | ![bisindeno thiophene 9] | |
| 2a: R⁵,R⁶ = H | 9a: R³–R⁹ = H | 50% |
| 2b: R⁵ = OCH₃ R⁶ = H | 9b: R³,R⁹ = OCH₃ R⁴,R⁸ = H | 40% |
| 2c: R⁵,R⁶ = OCH₃ | 9c: R³–R⁹ = OCH₃ | 23% |

TABLE 2-continued
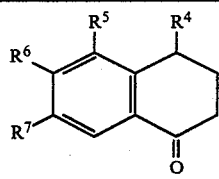 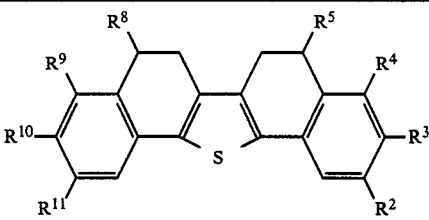
3a: R⁴-R⁷ = H
3b: R⁴ = CH₃
3c: R⁶ = OCH₃
3d: R⁵,R⁷ = CH
10a: R²-R¹¹ = H          53%
10b: R⁵,R⁸ = CH₃         50%
10c: R³,R¹⁰ = OCH₃       51%
10d: R²,R⁴,R⁹,R¹¹ = CH₃  30%
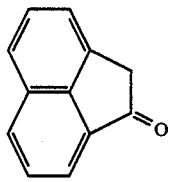 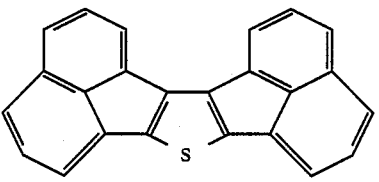
4                                    11                          40%
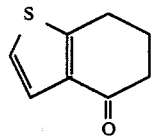 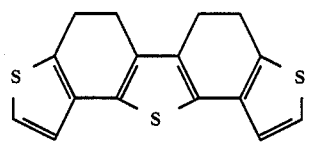
5                                    12                          50%
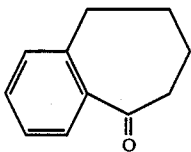 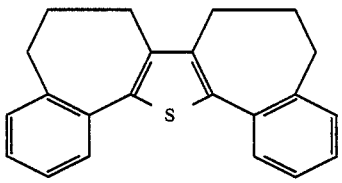
6                                    13                          25%
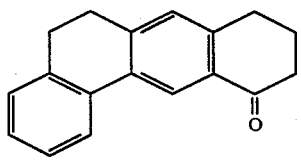 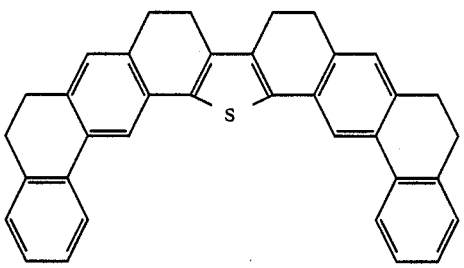
7                                    14                          54%
physical data
| Compound | M.P. °C. | Empirical formula (m.w.) | Calc. Found | Elementary analysis | | | ¹H—NMR (CDCl₃) δ = ppm | IR(KBr) ν = cm⁻¹ |
|---|---|---|---|---|---|---|---|---|
| | | | | C | H | S | | |
| 8 | 150-51(Ethanol) | | | | | | | 745 |
| 9a | 285(Cumene) | | | | | | | 750 |
| 9b | 290(Toluene) | C₂₀H₁₆O₂S (320.4) | | 74.98 74.35 | 5.03 5.02 | 10 10.2 | | 1240 |
| 9c | 274(Decomp) | C₂₂H₂₀O₄S (380.4) | | 69.45 71.79 | 5.30 5.69 | 8.48 9.11 | | 1250 |
| 10a | 230-32(Toluene) | C₂₀H₁₆S (288.4) | | 83.29 83.01 | 5.59 5.47 | 11.12 11.03 | 2.5-3.2 (m;8H,4CH₂), 7.1-7.7(m;8H arom) | 750 |
| 10b | 122-24(i-propanol) | C₂₂H₂₀S (316.4) | | 83.50 83.27 | 6.37 6.30 | 10.13 10.37 | 1.1-1.42 (d;6H,2CH₃), 2.15-3.5(m | 757 |

TABLE 2-continued

| | | | | | | |
|---|---|---|---|---|---|---|
| 10c | 222–24(Toluene) | C$_{22}$H$_{20}$O$_2$S (348.46) | | | 9.20 2.5–3.15 9.13 (m;8H,4CH$_2$), 3.8(s;6H,2CCH$_3$), 6.65–7.58m;6H arom) 6H,2CH$_2$,2CH), 7.1–7.7(m,8H arom) | 1240 |
| 10d | 222–24(Cyclohexane) | C$_{24}$H$_{24}$S (344.6) | 83.66 83.51 | 7.02 7.48 | 9.32 2.32(s; 9.19 12H,4CH$_3$), 2.62–3.2(m;8H,4CH) 6.8–7.48m,4H arom) | 847 |
| 11 | 278(Xylene) | | | | | 797 |
| 12 | 254–56(Glyme) | C$_{16}$H$_{12}$S$_3$ (300.46) | 63.96 63.85 | 4.03 4.02 | 32.01 3.07–3.72 32.00 (m;8H,4CH$_2$), 7.1–7.65(m;8H arom) | 808 |
| 13 | 159(Cyclohexane) | C$_{22}$H$_{20}$S (316.4) | 83.50 83.03 | 6.37 6.39 | 10.13 2.0–2.86 10.38 (m;12H,6CH$_2$), 7.1–7.6(m;8H arom) | 753 |
| 14 | 282–85(Cumene) | C$_{36}$H$_{28}$S (492.6) | 87.76 87.74 | 5.73 5.67 | 6.51 2.7–3.22 6.46 (m;16H,8CH$_2$), 7.0–8.0(m;12H arom) | 760 |

I claim:

1. A process for the production of a thiophene or b.d-ortho-fused thiophene, comprising:
   reacting an α-methylene ketone in a polar solvent with bromine to form a 2-bromo-1-ketone, separating the solvent out,
   directly reacting the formed 2-bromo-1-ketone with a sulphurising agent in a solvent to form a reaction product, and
   isolating the formed reaction product.

2. The process according to claim 1, wherein the α-methylene ketone is a unsubstituted or substituted aryl methyl ketone.

3. The process according to claim 2, wherein the aryl methyl ketone is acetophenone.

4. The process according to claim 1, wherein the α-methylene ketone is a unsubstituted substituted hydroaromatic 5-ring ketone, 6-ring ketone or 7-ring ketone.

5. The process according to claim 4, wherein the hydroaromatic ring ketone is a 1-indanone, a 1-acenaphthenone, tetrahydrobenzanthracenone or a 1-tetralone or a benzosuberone.

6. The process according to claim 1, wherein the α-methylene ketone is a unsubstituted or substituted hydroheteroaromatic ketone.

7. The process according to claim 6, wherein the hydroheteroaromatic ketone is a tetrahydrobenzothiophenone.

8. The process according to claim, wherein the α-methylene ketone is substituted by one or more linear or branched alkyl groups, methoxy groups, masked amino groups or carbonyl groups.

9. The process according to clam 1, wherein the polar solvent for the reactiobn with bromine is an alcohol, ether, glacial acetic acid, chloroform or carbon tetrachloride.

10. The process according to claim 9, wherein the solvent for the reaction with bromine is a low molecular weight alcohol (C$_{1-4}$).

11. The process according to claim 10, wherein methanol is used as the solvent.

12. The process according to claim 1, wherein a phosphorus-sulphur compound of the formula P$_4$S$_x$ is used as sulphurising agent, in which formula, x has the value 3, 5, 7, 9 or 10 and that an aromatic hydrocarbon or pyridine is used as solvent.

13. The process according to claim 12, wherein benzene, toluene and/or xylene is used as solvent for the reaction with the sulphurising agent,.

14. The process according to claim 12, wherein the molar ratio of sulphurising agent to ketone is in the range from 0 .1:1 to 1.5:1.

15. The process according to claim 1, wherein Lawessons reagent is used as sulphurising agent and an aromatic hydrocarbon or pyridine is used as solvent.

16. The process according to claim 15, wherein benzene, toluene or xylene or mixtures thereof is used as solvent for the reaction with the sulphurising agent.

17. The process according to claim 15, wherein the molar ratio of sulphurising agent to ketone is in the range from 0.5:1 to 1.5:1.

18. The process according to claim 1, wherein a phosphorus-sulphur compound of the formula P$_4$S$_x$, in which x has the value 3, 5, 7, 9 or 10, is used as sulphurising agent, in combination with Na$_2$S, NaHCO$_3$ or Na$_2$CO$_3$ as catalyst and a polar solvent.

19. The process according to claim 18, wherein the polar solvent is tetrahydrofuran, diethylene glycol dimethyl ether or ether.

20. The process according to claim 1, wherein silicon disulphide or boron sulphide (B$_2$S$_3$) is used as sulphurising agent and chloroform or an aromatic hydrocarbon is used as solvent.

21. The process according to claim 1, wherein 0,0-diethyl dithiophosphoric acid is used as sulphurising agent.

22. The process according to claim 1, wherein the reaction with the sulphurising agent is carried out under reflux conditions at temperatures up to 200° C.

* * * * *